(12) United States Patent
McIntosh

(10) Patent No.: US 10,321,861 B2
(45) Date of Patent: Jun. 18, 2019

(54) CALIBRATED PH SENSOR

(71) Applicant: Softcell Medical Limited, Aberdeen (GB)

(72) Inventor: Kirsty McIntosh, Aberdeen (GB)

(73) Assignee: SOFTCELL MEDICAL LIMITED, Aberdeen (GB)

( * ) Notice: Subject to any disclaimer, the term of this patent is extended or adjusted under 35 U.S.C. 154(b) by 583 days.

(21) Appl. No.: 14/407,861

(22) PCT Filed: Jun. 11, 2013

(86) PCT No.: PCT/GB2013/000257
§ 371 (c)(1),
(2) Date: Dec. 12, 2014

(87) PCT Pub. No.: WO2013/186513
PCT Pub. Date: Dec. 19, 2013

(65) Prior Publication Data
US 2015/0164395 A1    Jun. 18, 2015

(30) Foreign Application Priority Data

Jun. 13, 2012 (GB) .................................. 1210439.4

(51) Int. Cl.
*A61B 5/00* (2006.01)
*A61B 5/145* (2006.01)
(Continued)

(52) U.S. Cl.
CPC ........ *A61B 5/14539* (2013.01); *A61B 5/1473* (2013.01); *A61B 5/1495* (2013.01);
(Continued)

(58) Field of Classification Search
CPC ..... A61B 5/746; A61B 5/742; A61B 5/14539; A61B 5/1473; A61B 5/4848;
(Continued)

(56) References Cited

U.S. PATENT DOCUMENTS 3,719,576 A    3/1973  Macur
4,689,308 A *  8/1987  Gerhard ............ G01N 27/4165
                                                  436/18
(Continued)

FOREIGN PATENT DOCUMENTS

JP    2007-517195    6/2007
WO    WO-00/73763    12/2000
(Continued)

OTHER PUBLICATIONS

International Search Report and Written Opinion for PCT/GB2013/000257, dated May 12, 2014.

*Primary Examiner* — Tiffany Weston
*Assistant Examiner* — Tho Q Tran
(74) *Attorney, Agent, or Firm* — Foley & Lardner LLP

(57) ABSTRACT

The present invention relates to a pH sensor adapted to be inserted into all soft tissues, such as muscle, fat or other organs e.g. heart, lung, kidney, liver, pancreas, renal gland etc., comprising one or more of: a) means to provide sensor calibration performance information; b) a sensor dislodgement alert, providing an indication to the user if the pH reading falls outside a predetermined range; c) an alert to indicate that the sensor has exceeded its usage period; and d) an alert to indicate that the sensor had exceeded its shelf life. There is also provided a method of assessing the efficacy of a treatment regime comprising the steps of determining any change in the pH of the soft tissue during treatment, where any change in the pH towards the preferred range for the tissue type is indicative of an effective treatment regime and any change in the pH away from the preferred range for the tissue type is indicative of a worsening in the condition of the tissue, and thus an ineffective treatment regime.

18 Claims, 1 Drawing Sheet

(51) Int. Cl.
*A61B 5/1495* (2006.01)
*A61B 5/1473* (2006.01)

(52) U.S. Cl.
CPC .......... *A61B 5/4848* (2013.01); *A61B 5/7275* (2013.01); *A61B 5/7282* (2013.01); *A61B 5/742* (2013.01); *A61B 5/746* (2013.01); *A61B 5/14503* (2013.01); *A61B 5/4519* (2013.01); *A61B 2560/028* (2013.01); *A61B 2560/0228* (2013.01); *A61B 2560/0276* (2013.01); *A61B 2562/242* (2013.01)

(58) Field of Classification Search
CPC ... A61B 5/7275; A61B 5/7282; A61B 5/1495; A61B 2562/242; A61B 2560/0276; A61B 5/14503; A61B 5/4519; A61B 2560/0228; A61B 2560/028
See application file for complete search history.

(56) References Cited

U.S. PATENT DOCUMENTS

| | | | | |
|---|---|---|---|---|
| 4,834,101 | A | | 5/1989 | Collison et al. |
| 5,234,835 | A | | 8/1993 | Nestor et al. |
| 5,280,548 | A | * | 1/1994 | Atwater ............. G01N 21/6428 385/12 |
| 5,325,853 | A | * | 7/1994 | Morris ............... G01N 27/4165 204/403.02 |
| 5,354,449 | A | * | 10/1994 | Band ................. A61B 5/14539 204/418 |
| 6,101,406 | A | * | 8/2000 | Hacker ............. A61B 5/14557 356/39 |
| 6,567,679 | B1 | | 5/2003 | Khuri et al. |
| 6,600,941 | B1 | | 7/2003 | Khuri |
| 7,813,781 | B2 | | 10/2010 | Johnstone |
| 8,990,018 | B2 | * | 3/2015 | Dijksman ............. A61B 5/073 206/538 |
| 2003/0040665 | A1 | * | 2/2003 | Khuri ................ A61B 5/14539 600/345 |
| 2003/0109822 | A1 | * | 6/2003 | Barnett ............. A61B 5/14542 604/27 |
| 2004/0138542 | A1 | | 7/2004 | Khuri et al. |
| 2006/0015025 | A1 | * | 1/2006 | Johnstone ................ A61B 5/03 600/361 |
| 2007/0163881 | A1 | * | 7/2007 | Pechstein ........... G01N 27/4148 204/406 |
| 2010/0033188 | A1 | * | 2/2010 | Rieth ....................... A61B 5/01 324/438 |
| 2011/0077480 | A1 | * | 3/2011 | Bloom ............. A61B 5/14532 600/310 |
| 2011/0112442 | A1 | * | 5/2011 | Meger ................. A61B 5/0002 600/595 |
| 2011/0236962 | A1 | * | 9/2011 | Loebbert ................ C12M 23/28 435/287.1 |
| 2015/0114836 | A1 | * | 4/2015 | Clark ................... G01N 27/302 204/403.02 |

FOREIGN PATENT DOCUMENTS

WO     WO-00/74753 A1    12/2000
WO     WO-2005/061995       7/2005

* cited by examiner

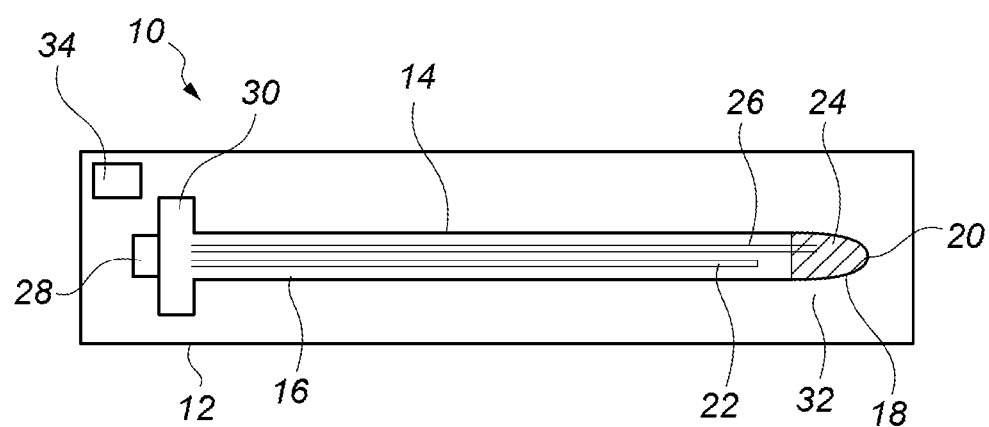

CALIBRATED PH SENSOR

CROSS REFERENCE TO RELATED APPLICATIONS

This application is a national stage application of International Application Serial No. PCT/GB2013/000257, filed on Jun. 11, 2013, which in turn claims the benefit of GB application 1210439.4, filed on Jun. 13, 2012, both of which are hereby incorporated by reference in their entirety, for any and all purposes.

The present invention relates to a pH sensor and its use in the assessment of the health or condition of soft tissues in vivo, composite cell and tissue cultures (explants), and cell cultures both grown in vitro. The use of the pH sensor in the diagnosis of medical conditions is also provided. In particular the present invention provides a pH meter including means to assess the accuracy of the sensor immediately prior to use, and/or means to alert the user if the pH sensor has been dislodged from the body during use.

BACKGROUND TO THE INVENTION

The use of pH sensors in the diagnosis of particular conditions, in particular ischaemia is known. U.S. Pat. No. 7,813,781 discloses a method and apparatus for determining information concerning ischaemia using a pH sensor. Information may be determined about ischaemia caused by a number of factors, including acute compartment syndrome, vascular disorders, diseases or conditions that affect tissue perfusion including surgical procedures, and generalised diseases or conditions e.g. septicaemia, significant blood loss and significant bodily fluid loss resulting for example from skin burns.

U.S. Pat. No. 6,600,941 and U.S. Pat. No. 6,567,679 both disclose the use of pH measurements of tissue as a system for controlling diagnostic and/or surgical procedures. An apparatus used to perform tissue pH measurements is also disclosed. Real time tissue pH measurements can be used as a method to determine ischaemic segments of the tissue and provide the user with courses of conduct during and after a surgical procedure. When ischaemia is found to be present in a tissue, a user can affect an optimal delivery of preservation fluids to the site of interest and/or use pharmacological methods to improve tissue perfusion and/or effect a change in the conduct of a surgical procedure to normalise the pH within the site of interest.

In general, pH sensors are manufactured several months before use. The pH sensors and associated probes should be stored and used under suitable conditions (−5 to 40 C, 30 to 80% humidity). However, if the conditions for storage or use are unsuitable, the accuracy of the pH sensor may be adversely affected.

From current designs it is known to calibrate pH sensors immediately prior to use. In particular it is known to calibrate pH sensors with at least two standard buffer solutions that span a considerable portion of the range of pH values to be measured (e.g. buffers at pH 4 and pH 10). However, pH sensors may be used in the diagnosis of life threatening conditions such as ischaemia. For such uses, pH sensors must be available for immediate use—where a patient is suffering from a potentially fatal or serious condition, there is insufficient time for complex calibration procedures immediately prior to use. In addition, complex calibration procedures increase the likelihood of contamination and the sterility of the sensor would be compromised.

STATEMENT OF INVENTION

According to a first aspect of the present invention there is provided a pH sensor adapted to be inserted into all soft tissues, such as muscle, fat or other organs e.g. heart, lung, kidney, liver, pancreas, renal gland etc., comprising one or more of:
  a) means to provide sensor calibration performance information;
  b) a sensor dislodgement alert, providing an indication to the user if the pH reading falls outside a predetermined range;
  c) an alert to indicate that the sensor has exceeded its usage period; and
  d) an alert to indicate that the sensor had exceeded its shelf life.

According to a second aspect of the present invention there is provided a method of determining the pH in a soft tissue comprising the steps of inserting the pH sensor disclosed above into the soft tissue of interest.

According to a third aspect of the present invention there is provided a method of determining information concerning the condition of the soft tissue of interest comprising the steps of determining the pH of the soft tissue (preferably over a prolonged period of, for example, 70 to 100 hours) with the pH sensor as described above.

According to a fourth aspect of the present invention there is provided a method of assessing the efficacy of a treatment regime comprising the steps of determining any change in the pH of the soft tissue during treatment, where any change in the pH towards the preferred range for the tissue type is indicative of an effective treatment regime and any change in the pH away from the preferred range for the tissue type is indicative of a worsening in the condition of the tissue, and thus an ineffective treatment regime.

According to a fifth aspect of the present invention there is provided a method of diagnosis of a medical condition, in particular ischaemia, in a patient comprising the steps of determining the pH of soft tissues of the patient using the pH sensor as described above, and comparing the pH with a predetermined range indicative of the medical condition. It should be noted that with certain conditions or as a result of drug ingestion or certain pharmacological treatments that a metabolic acidosis or alkalosis can also occur.

According to a sixth aspect of the present invention there is provided the sensor as described above for use in therapy or diagnosis.

According to a seventh aspect of the present invention there is provided the sensor as described above for use in the diagnosis of a medical condition affecting soft tissue, in particular ischaemia.

DETAILED DESCRIPTION pH Sensor

The pH of a solution indicates how acidic or basic (alkaline) it is. The pH term translates the values of the hydrogen ion concentration—which ordinarily ranges between about 1 and 10×−14 gram-equivalents per liter—into a number between 0 and 14.

A pH sensor is an electronic instrument measuring the pH of a liquid. The pH is generally measured by measuring the voltage generated through the flow of cations from the test sample to an electrode within the pH sensor. Generally the pH sensor is connected to a meter which converts the voltage measurement to a pH reading in pH units, and displays the pH reading.

The pH sensor generally comprises:
- a shaft,
- a tip at one end of the shaft comprising a sensing membrane having an internal surface and an external surface,
- a reference electrode which is either internal i.e. in close proximity to the tip of the sensor, or external, i.e. distant to the tip of the sensor,
- an internal solution contacting the internal surface of the sensing membrane,
- a measuring electrode extending into the internal solution, and
- a connection means suitable for connecting the sensor to a meter.

In use, the tip of the pH sensor and the reference electrode are immersed into the sample to be tested, which is generally in the form of a liquid (the external liquid) or cells surrounded by a liquid medium as exists in all biological tissues, or the liquid medium that sustains cultured composite cell and tissue cultures (explants), and cell cultures both grown in vitro. In some embodiments the sample may be a gas. The internal and external surfaces of the sensing membrane are protonated by H+ ions from the internal solution and the external liquid respectively until equilibrium is reached. The internal and external surfaces of the sensing membrane are charged by the adsorbed protons, resulting in a potential between the two surfaces of the sensing membrane which is directly proportional to the pH difference between the internal solution and the external liquid. In use, the pH sensor is connected to a meter which converts and displays this potential in pH units. For each pH sensor, the conversion between pH units and voltage is known. As an example, for some pH sensors, a pH unit is equivalent to about 0.06 volts. However, different pH sensors may have different conversions.

The pH sensor generally also includes a reference electrode which provides a stable potential against which the measuring electrode can be compared. The reference electrode is surrounded by a reference solution, at a known pH. The reference solution is able to exchange ions with the internal solution, generally via a porous separator forming a low resistance connection to the test liquid. Alternatively, the internal reference electrode may not be able to exchange ions with the internal solution but may nonetheless be in close proximity to the tip of the pH sensor.

Alternatively, the reference electrode may be exterior to the pH sensor.

The sensing membrane forms an ion selective barrier, screening out hydrogen ions from all of the other ions in the external liquid. The sensing membrane is generally formed from pH sensitive glass or plastic (in particular, epoxy or polymer based plastics). The sensing membrane is typically in the form of a bulb formed from pH sensitive glass.

The pH of the internal solution and the reference solution is generally known, and is typically about pH 6 to 7. According to one embodiment, the pH of the internal solution and the reference solution is around 6.4. However, different pH sensors may vary in this regard. The internal solution and/or the reference solution may be a potassium chloride solution (typically 0.1 mol/L). However, other suitable solutions are known in the art and may be used.

Preferably the pH of the internal solution is about pH 6.2 to 6.6, typically about 6.4.

The measuring electrode and/or the reference electrode is H+ ion sensitive, and is typically formed from silver, generally silver coated with silver chloride.

The porous separator provides a junction between the reference solution and the internal solution, and is generally formed from or comprises ceramic, asbestos or quartz fibre.

Alternatively, other forms of pH sensor may be used in accordance with the present invention. These other families of pH sensors include: antimony, ion sensitive field effect transistor (ISFET), or ion selective electrodes. In particular pH sensors such as those sold under the trade names, Oakfield Instruments (antimony), Biocontrol (ISFET) may be used.

In general, pH sensors are calibrated immediately prior to use using buffers of known pH. However, using our new technology, calibration may be undertaken in the factory and the calibration information stored within the sensor, for instance the sensor may include a chip detailing such information. The performance of a pH sensor may differ according to the temperature and humidity conditions at which the sensor is used. Preferably, numerous sensors manufactured at the same time according to the same specification are calibrated under a variety of predetermined temperatures and humidity conditions. An algorithm may then be generated concerning the performance of multiple sensors belonging to the same "family". This algorithm may be stored in association with the sensor, for instance, it may be included on a chip which forms part of the sensor or it may be stored on the meter associated with the sensors. Alternatively, it may be advantageous to store the individual parameters of each probe with respect to temperature and humidity on a chip which forms part of each sensor.

Means to Provide Sensor Calibration Performance Information

According to one embodiment, the pH sensor of the present invention includes means to provide sensor calibration performance information. The pH sensor may include a calibration indicator composition, and an indication of the pH of this composition. Immediately prior to use, the pH sensor of the present invention may be contacted with the calibration indicator composition, and the reading provided can be compared to the indication of the pH of the calibration indicator composition provided in association with the pH sensor. A quick, straight forward check that the calibration of the pH sensor is accurate is thus provided, giving reassurance that the calibration hasn't drifted during storage or has been damaged.

The calibration check is both quick and easy, providing an indication of whether the pH sensor is accurate immediately prior to use. The check itself is very quick, generally taking 5 minutes or less, typically 1 minute or less. As such, the pH sensor of the present invention is of particular utility in emergency situations. The calibration check is also suitable for use by users without medical training as it is very simple which is particularly useful for home users.

Typically, the pH sensor is plugged into the meter, the calibration check is conducted and the pH sensor is then used if the calibration check shows that the pH sensor is accurate. The calibration check is generally performed 5 minutes or less before use of the pH sensor.

According to one embodiment, the time period between removal of the pH sensor from its sterile environment and use is five minutes or less, where the calibration performance check is performed during this time.

The calibration indicator composition may be an integral part of the pH sensor package, or may be separate to the pH sensor. Preferably, the calibration indicator composition forms part of the pH sensor package.

The pH sensor of the present invention would generally only include one calibration indicator composition. As such, the pH sensor of the present invention would not generally enable full calibration of the pH sensor, and those pH sensors which do not provide an accurate pH reading for the calibration indicator composition would be discarded, or set aside for full calibration. Generally, those pH sensors which do not provide an accurate pH reading would be discarded.

Where the pH sensor comprises means to provide calibration performance information, the pH sensor may comprise a coating which totally or partially covers the sensing membrane, said coating comprising a calibration indicator composition at a known pH.

According to one embodiment, the calibration indicator composition may be in the form of a hydrogel, effectively trapping a thin layer of water of known pH next to the sensing membrane.

Where the pH sensor comprises means to provide calibration performance information, the sensor may be in the form of a sensor package, comprising the pH sensor as described above, surrounded by a closed housing suitable for maintaining the sterility of the pH sensor, the housing generally including a calibration indicator composition at a known pH, wherein the calibration indicator composition contacts the sensing membrane of the pH sensor, and the sensor package includes an indication of the pH of the calibration indicator composition.

As part of the manufacturing process, pH sensors can be calibrated prior to packaging and sterilisation. In general, using modern sensor technology, approximately 80 to 90% of sensors manufactured work accurately following strict manufacturing processes and calibration checks are undertaken to confirm sensor accuracy. However, 10 to 20% of all sensors manufactured do not operate with sufficient accuracy when calibration checks are performed. An indication of which sensors are not of sufficient accuracy, and require further calibration prior to use would be very useful in maximising the accuracy of the pH sensors. According to one embodiment, pH sensors which do not provide an accurate pH reading according to the calibration performance check, would be discarded.

In addition, the accuracy of pH sensors may be affected after manufacture. In general, pH sensors are stored for several months prior to use. Even those sensors which operate accurately following manufacture may not operate with sufficient accuracy upon eventual use. The accuracy of pH sensors may drift from accurate values upon storage, in particular for those sensors which have not been stored under optimal conditions. In particular, storage of pH sensors under incorrect temperature or moisture conditions may affect their accuracy. The calibration performance check provides an indication of which pH sensors are not operating with sufficient accuracy. Generally such sensors are discarded. However, according to one embodiment, such sensors may under further calibration to improve their accuracy.

It is known to calibrate pH sensors immediately prior to use. In particular it is known to calibrate pH sensors with at least two standard buffer solutions that span the range of pH values to be measured (e.g. buffers at pH 4 and pH 10). However, pH sensors may be used in the diagnosis of life threatening or serious conditions such as ischaemia. For such uses, pH sensors must be available for immediate use—where a patient is suffering from a potentially fatal condition there is not time for a complex calibration procedure immediately prior to use. Complex calibration procedures increase the likelihood of contamination and thus increase the likelihood of the sterility of the sensor being compromised.

There has recently been a move towards allowing patients to be treated at home wherever possible. This results in patients themselves providing readings to remote healthcare professionals. Patients would not generally have the means or the experience to calibrate scientific equipment such as pH sensors themselves.

The sensor of the present invention provides an indication of the accuracy of the sensor immediately prior to use. The sensor is connected to a meter immediately after removal from the closed housing. The initial pH reading is noted and compared with the indication of the pH of the calibration indicator composition provided with the sensor package, typically as part of the sensor package. If the initial reading is approximately the same as the predetermined value, the sensor may be used with confidence. If the initial reading does not provide an accurate reading compared to the predetermined value, the sensor is generally discarded. Generally a difference of 10% of the predetermined value will be tolerated, typically 5%, advantageously 1% or less.

The sensor of the present invention provides an indication of the accuracy of the sensor immediately prior to use. As well as allowing immediate use of the pH sensor with confidence, this promotes the use of the pH sensor by inexperienced users. Calibrating scientific equipment can be expensive and time consuming, and the pH sensor of the present invention allows these efforts to be minimised, or where the inaccurate sensors are retained rather than being discarded, calibration is minimised for those sensors which require calibration. Preferably, the pH sensor is discarded if it is not performing with sufficient accuracy.

The calibration indicator composition is typically suitable for maintaining the hydration of the sensing membrane of the pH sensor. For some models of currently available pH sensors, the sensing membrane must be stored in the presence of fluids, in particular fluids containing hydrogen ions, to avoid dehydration which may alter the porosity of the sensing membrane. This can lead to the pH sensor not functioning properly or potentially ceasing to function altogether.

Other currently available pH sensors do not require the sensing membrane to be maintained in a hydrated form. For such embodiments, it would not be necessary for the calibration indicator composition to maintain the hydration of the sensing membrane.

The calibration indicator composition is generally in the form of a liquid, solution, suspension, paste, gel, or foam. Advantageously, the calibration indicator composition is in the form of a gel.

According to one embodiment, the calibration indicator composition has a pH of 6 to 7.5, typically 6 to 6.5, suitably 6.3 to 6.5, preferably about 6.4.

The calibration indicator composition generally has a pH approximately the same as that of the internal solution of the pH sensor. Where the pH of the calibration indicator composition is approximately the same as that of the internal solution, the cation movement across the pH sensing membrane is neutral, that is the movement of cations from the internal solution into the calibration indicator composition is approximately the same as the movement of cations from the calibration indicator composition to the internal solution. As such, the associated potential across the sensing membrane is approximately zero for accurately calibrated pH sensors.

If the calibration of the pH sensor is inaccurate, this will be particularly evident where the pH of the calibration indicator composition is approximately equal to that of the internal solution (generally at a pH of about 6.4) as the potential across the sensing membrane should be about zero for such embodiments. Storing the sensing membrane in contact with a calibration indicator composition having a pH about the same as the pH of the internal solution of the pH sensor provides a good indication of whether the calibration of the pH sensor is accurate.

The means to provide calibration performance information is generally integral to the sensor package. The calibration indicator composition is typically within the closed housing, and generally contacts the sensing membrane during storage. An indication of the pH of the calibration indicator composition may be provided on or in the closed housing.

According to one embodiment, the calibration indicator composition is in the form of a buffered gel, for instance a potassium-containing buffered gel such as that sold under the trade name Friskolyte.

Sensor Dislodgement Alert

As noted above, the pH sensor of the present invention may include a sensor dislodgement alert, providing an indication to the user if the pH reading falls outside a predetermined range.

In use, the tip of the pH sensor is generally inserted into the tissue of interest, the shaft of the pH sensor generally extends out of the patient, and the pH sensor is held in place with a bandage or other form of dressing. Generally, pH sensors are used to take continuous measurements over several hours or days, in order to provide an indication of the changes or trends in pH over time. This can provide an indication of the health or condition of the tissue tested, and thus provides a measure of the effectiveness of treatment. Where pH is measured by a healthcare practitioner, the healthcare practitioner generally reviews the pH measurements collected at spaced intervals. As the point of entry of the pH sensor into the patient's body is generally covered by a dressing, the pH sensor may be dislodged from the body without observation. In such circumstances, the pH sensor would be under the dressing but outside the body. Readings of pH would continue to be taken but would be outside the range expected from human/mammalian tissues. It is likely that a healthcare practitioner would be able to identify the pH readings as aberrant and investigate whether the pH sensor had been dislodged. However, medical practitioners generally only review the pH readings at spaced intervals, and the readings from dislodgement until reinsertion of the pH sensor into the body of the patient would be meaningless. Trends in pH would be more difficult to identify, and the time taken for a measure of the effectiveness of treatment to be provided would be increased.

The sensor of the present invention may be used by unskilled personnel, including the patient themselves. Such users would not generally understand the significance of aberrant readings, and would not immediately investigate whether the sensor had been dislodged.

The sensor of the present invention may provide an alert of sensor dislodgement, allowing a medical practitioner to investigate soon after dislodgement has occurred. The alert is provided if the pH reading falls outside a predetermined range.

The predetermined range would be dependent on the type of tissue the pH sensor is inserted into. For instance, the pH range of fat differs considerably from the pH range of the kidney. In addition, the pH range which may be associated with the kidney or the gastrointestinal tract is very wide compared to the pH range which may be associated with tissue such as muscle or fat.

As noted above, the predetermined pH range is dependent on the tissue of interest. However, in general the predetermined pH range is 5 to 8, typically 6.0-7.2

As noted above, the pH sensor provides an indication of the potential across the sensing membrane. The pH meter then converts this into a reading of pH. Each pH sensor has an associated rate for converting the potential across the sensing membrane to a pH reading, and the conversion rate would be known for each pH sensor. Some currently known pH sensors convert a potential of around 0.06V to one pH unit. However, this conversion rate may differ between pH sensors. The potential at which the alert will start will be dependent on the pH sensor and its conversion rate. According to one embodiment, the alert may start where the potential across the sensing membrane is less than 0.3V, or where the potential is greater than 0.48V.

The alert may be visual or audible, or both visual and audible. Generally the alert starts within 1 minute or less of the pH reading falling outside the pH range, typically 30 seconds or less, suitably within 10 seconds or less.

The alert generally has a duration of 5 to 10 minutes. For such a duration, the audible and visual aspects of the alert may be continuous. Where the alert is both audible and visual, the audible aspect of the alert may stop after such duration and the visual aspect may continue until the pH reading is within the predetermined range.

The alert may be repeated, typically at intervals while the pH reading remains outside the predetermined range.

Alert to indicate that the Sensor has exceeded its Usage Period

As noted above, the pH sensor of the present invention may comprise an alert to indicate that the sensor has exceeded, or is about to exceed its usage period.

A pH sensor can remain inserted into the tissue of interest for extended periods of time. If a pH sensor remains in a patient's body for too long, the chance of infection developing around the sensor where it penetrates the skin is greatly increased. Generally, following expiry of the usage period a new sensor should be inserted into a different but neighbouring site in an effort to minimise the risk of localised infection. A pH sensor may be used to take continual readings, thus providing an indication of the changes or trends in pH over time. Medical practitioners tend to review the readings at spaced intervals. Different medical practitioners will review the readings over the time the pH sensor is inserted and it is easy for the medical practitioners not to realise how long an individual pH sensor has been inserted into the patient. As such, pH sensors may be inserted into a patient for far longer than is optimal, increasing the risk of infection accordingly.

The sensor of the present invention may include an alert to indicate that the sensor has exceeded its usage period. The time period for insertion of the sensor into the patient is minimised, thus minimising the risk of infection.

In general the usage period is 100 hours, typically 90 hours, suitably 80 hours. According to one embodiment, the usage period is 72 hours.

The usage period is generally measured from the point that the pH sensor and meter are connected, immediately before it is inserted into the tissue of interest. Generally, the pH sensor is inserted into the tissue of interest within 2 minutes of the pH sensor being connected to the meter, typically within 1 minute of connection, preferably within 30 seconds of connection.

According to one embodiment, the alert begins 1 hour prior to expiry of the usage period, suitably 30 minutes, typically 10 minutes prior to expiry of the usage period.

Alert to indicate that the Sensor has exceeded its Shelf Life

As noted above, the pH sensor of the present invention may comprise an alert to indicate that the sensor has exceeded, or is about to exceed its shelf life.

Although pH sensors are calibrated during manufacture, the accuracy of their calibration reduces upon storage, in particular if the storage of the pH sensor is under conditions that are suboptimal and may affect the porosity of the sensing membrane. With some designs the sensing membrane of pH sensors must be kept in contact with fluids, in particular fluids containing hydrogen ions in order to function properly. With other designs, hydration of the sensing membrane is not necessary. As the time period from manufacture to use increases, the risk of sensor inaccuracy also increases.

The shelf life of the sensor is generally one year, suitably two years. According to one embodiment, the shelf life of the sensor is three years.

The shelf life is generally measured from manufacture, in particular from sterilisation of the sensor.

According to one embodiment, the alert begins one week from expiry of the shelf life, typically 3 days, suitably one day from expiry of the shelf life.

The alert to indicate that the sensor has exceeded its usage period or its shelf life may be visual or audible, or both visual and audible. Generally the alert starts immediately after being connected to the meter.

In one embodiment, after the shelf life has been exceeded, the sensor, after being connected to the meter, will not permit pH to be recorded.

Generally where the alert indicates that the sensor has exceeded its shelf life or usage period, the alert is both audible and visual.

The alert generally has a duration of 5 to 10 minutes. For such a duration, the audible and visual aspects of the alert may be continuous. Where the alert is both audible and visual, the audible aspect of the alert may stop after such duration and the visual aspect may continue until the alert is overridden. Alternatively, or additionally the alert may be repeated at intervals until it is overridden. Advantageously, where the alert is overridden, the sensor provides an indication of this and the meter records this event.

Where the sensor includes the alert indicating that the sensor has exceeded its usage period or shelf life as described above, the sensor generally includes a clock mechanism, to countdown the usage period/shelf life. The clock mechanism is generally linked to the alert. Where the clock mechanism indicates that the usage period/shelf life has expired, the alert starts once the pH sensor is plugged into the meter.

Preferred Embodiments

Preferably the sensor of the present invention comprises means to provide calibration performance information.

According to a further embodiment, the sensor of the present invention advantageously comprises a sensor dislodgement alert.

The sensor of the present invention may comprise means to provide calibration performance information, and a sensor dislodgement alert. In addition, the sensor of the present invention may comprise an alert to indicate that the usage period, and/or shelf life has expired, or is about to expire.

According to one embodiment, the sensor may also comprise means to record information, for instance one or more of patient details, the date and time of use and the highest and lowest pH values recorded during the use. The means to record the information may be in the form of a chip, in particular the connection means for connecting the sensor to a meter may comprise the chip.

Measurement of pH of Soft Tissue

According to one aspect of the present invention, there is provided the use of a pH sensor as described above in a method of therapy or diagnosis.

The method of diagnosis may be in vivo or in vitro.

According to an aspect of the present invention there is provided a method of determining the pH in a soft tissue comprising the steps of inserting the pH sensor disclosed above into the soft tissue of interest.

The soft tissue is generally muscle (skeletal or cardiac) or fat, preferably muscle, including muscle adjacent to a fracture site or the muscles contained within the limbs (skeletal) or heart (cardiac) although other organs e.g. brain, lung, kidney, liver, pancreas, renal gland etc. could also be monitored. The sensor is typically inserted until the tip of the sensor is contained within the soft tissue of interest.

The soft tissues are generally the soft tissues of a human or animal, in particular a mammal.

The angle of insertion of the sensor is generally approximately between 30-45 degrees to the surface of the skin or tissue of interest.

Measurements of pH may be taken at regular intervals, for instance every few seconds up to 1 minute.

Method of Determining the Condition of Soft Tissue

According to a third aspect of the present invention there is provided a method of determining information concerning the condition of soft tissues comprising the steps of determining the pH of the soft tissue of interest (preferably over a prolonged period, for example, 70 to 100 hours) with the pH sensor as described above.

Typically, the trend of the change in pH is assessed over a prolonged period (for example several hours up to 5 days). Where the trend of pH is to move towards the preferred range for the particular type of soft tissue under investigation, the condition of the soft tissue is deemed to be improving. Where the trend of the pH is to move away from the preferred range for the particular type of soft tissue tested, the condition of the soft tissue is deemed to be declining.

The preferred pH range for muscle of the arms and legs (skeletal muscle) is 5.5-7.5

The preferred pH range for heart muscle (cardiac) is 5.5-7.5

The preferred pH range for fat is 5.5-7.5

According to a further aspect of the present invention there is provided a method of assessing the efficacy of a treatment regime comprising the steps of determining any change in the pH of the tissue of interest during treatment, where any change in the pH towards the preferred range for the tissue type is indicative of an effective treatment regime and any change in the pH away from the preferred range for the tissue type is indicative of a worsening in the condition of the tissue, and thus an ineffective treatment regime.

The treatment regime may include manipulation of the tissue, surgical treatments or the administration of pharmacological agents.

Method of Diagnosis

According to a fifth aspect of the present invention there is provided a method of diagnosis of a medical condition, in particular ischaemia, in a patient comprising the steps of determining the pH of soft tissue of the patient using the pH sensor as described above, comparing the pH with a predetermined range indicative of the medical condition.

As noted above, the normal pH range for heart muscle, skeletal muscle and fat is similar although the normal pH of other organs generally differs. In particular, the kidney (especially the central part of the kidney), and the gastro-intestinal tract can have wide pH ranges.

The method of diagnosis may include determining the pH of the soft tissue and determining whether the pH falls outside the normal pH range for that tissue type.

The method may include determining several other parameters that may add additional information, for instance the pressure and temperature of the soft tissue of interest.

Conditions which may be diagnosed include acute compartment syndrome, vascular insufficiency, traumatic or surgical disruption of the blood supply to the tissues of interest, septicaemia, extensive blood loss or extensive fluid loss e.g. secondary to skin burns.

The method of diagnosis may be in vivo or in vitro.

FIG. 1 shows a pH sensor package according to the present invention. The pH sensor package (10) includes a pH sensor (14) adapted to be inserted into soft tissue, such as muscle, fat or other organs, and a closed housing (12). The pH sensor (14) comprises a shaft (16), a tip (18) at one end of the shaft (16) the tip (18) comprising a sensing membrane (20) having an internal surface and an external surface, and an internal solution (24) contacting the internal surface of the sensing membrane (20). There is provided a reference electrode (22) and a measuring electrode (26) extending into the internal solution (24). There is also provided a connection means (28) suitable for connecting the pH sensor (14) to a meter. The pH sensor package (10) includes a means (30) to store calibration performance information of the pH sensor (14) at the time of manufacture thereof, wherein the means (30) to store calibration performance information includes calibration performance information comprises details of the individual performance parameters of the pH sensor (14) at different temperatures and humidities at the time of manufacture of the pH sensor (14). The pH sensor (14) is surrounded by the closed housing (12) suitable for maintaining the sterility of the pH sensor (14), the closed housing (12) includes a calibration indicator composition (32) at a known pH, wherein the calibration indicator composition (32) contacts the sensing membrane (20) of the pH sensor (14), and an indication (34) of the pH of the calibration indicator composition (32) is provided.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Throughout the description and claims of this specification, the words "comprise" and "contain" and variations of the words, for example "comprising" and "comprises", mean "including but not limited to", and are not intended to (and do not) exclude other moieties, additives, components, integers or steps.

Generally the term "approximately" is intended to encompass a range of 10% or less of any numerical value to which it is applied.

Further aspects and embodiments of the invention are set forth in the following description and claims.

While various embodiments of the present invention have been described above, it should be understood that they have been presented by way of example only, and not limitation. Thus, the breadth and scope of the present invention should not be limited by any of the above-described exemplary embodiments, but should instead be defined only in accordance with the following claims and their equivalents. All documents, including webpages, cited herein are incorporated in their entirety by reference.

The invention claimed is:

1. A pH sensor package comprising a pH sensor adapted to be inserted into soft tissue, means to store calibration performance information of the pH sensor at a time of manufacture thereof, one or more calibration indicator compositions comprising a first calibration indicator composition, an indication associated with the first calibration indicator composition, and a closed housing;
    wherein the pH sensor comprises:
        a shaft,
        a tip at one end of the shaft comprising a sensing membrane having an internal surface and an external surface,
        a reference electrode,
        an internal solution contacting the internal surface of the sensing membrane,
        a measuring electrode extending into the internal solution, and
        a connection means suitable for connecting the sensor to a meter;
    wherein the means to store calibration performance information comprises calibration performance information comprising details of individual performance parameters of the pH sensor at different temperatures at the time of manufacture;
    wherein the pH sensor is surrounded by the closed housing, and the closed housing is suitable for maintaining the sterility of the pH sensor;
    wherein the first calibration indicator composition is at a first pH;
    wherein the indication conveys the first pH of the first calibration indicator composition; and
    wherein each of the one or more calibration indicator compositions is maintained separate from the pH sensor in the pH sensor package.

2. The pH sensor package as claimed in claim 1, wherein the first calibration indicator composition is in the form of a buffered gel.

3. The pH sensor package as claimed in claim 1, wherein the first calibration indicator composition is in the form of a hydrogel coating.

4. The pH sensor package as claimed in claim 1, wherein the first pH is in the range of 6 to 7.5.

5. The pH sensor package as claimed in claim 1, wherein the indication is provided integrally to the sensor package.

6. The pH sensor package as claimed in claim 1, wherein the means to store performance information is in the form of a chip including an algorithm including information of the performance of the pH sensor at the time of manufacture, under different temperatures and humidities.

7. The pH sensor package as claimed in claim 1, further comprising a pH sensor dislodgement alert;
wherein the pH sensor is configured to determine a second pH proximate the sensing membrane; and
wherein the pH sensor dislodgement alert is configured to be activated in response to detecting the second pH of the first calibration indicator composition falling outside of a predetermined pH range.

8. The pH sensor package as claimed in claim 7, wherein the predetermined pH range is 5.0 to 8.0.

9. The pH sensor package as claimed in claim 7, wherein activation of the pH sensor dislodgment alert causes a visual alert and an audible alert to be broadcast.

10. The pH sensor package as claimed in claim 7, wherein the pH sensor dislodgment alert is activated within 1 minute or less of detecting the second pH of the first calibration indicator composition failing outside of the predetermined pH range.

11. The pH sensor package as claimed in claim 1, further comprising an alert;
wherein the alert is configured to be activated to convey that the pH sensor has exceeded, or is about to exceed, a usage period associated with the pH sensor.

12. The pH sensor package as claimed in claim 11, wherein the usage period is 72 hours from connection of the pH sensor to a meter.

13. The pH sensor package as claimed in claim 11, wherein the alert is configured to be activated 30 minutes prior to expiry of the usage period.

14. The pH sensor package as claimed in claim 1, further comprising an alert;
wherein the alert is configured to be activated to convey that the pH sensor has exceeded, or is about to exceed a shelf life associated with the pH sensor.

15. The pH sensor package as claimed in claim 14, wherein the shelf life is 1 year from the time of manufacture.

16. The pH sensor package as claimed in claim 14, wherein the shelf life is 3 years from the time of manufacture.

17. The pH sensor package as claimed in claim 14, wherein the alert is configured to be activated immediately after being connected to a meter if the pH sensor has exceeded, or is about to exceed, the shelf life.

18. The pH sensor package as claimed in claim 11, wherein activation of the alert causes a visual alert and an audible alert to be provided.

* * * * *